United States Patent
Park

(10) Patent No.: US 8,035,090 B2
(45) Date of Patent: Oct. 11, 2011

(54) STERILIZER FOR DENTAL CONTAMINANT

(75) Inventor: Heung Sik Park, Busan (KR)

(73) Assignee: C.P. Co (KR)

( * ) Notice: Subject to any disclaimer, the term of this patent is extended or adjusted under 35 U.S.C. 154(b) by 245 days.

(21) Appl. No.: 12/445,252

(22) PCT Filed: Oct. 9, 2007

(86) PCT No.: PCT/KR2007/004907
§ 371 (c)(1),
(2), (4) Date: Apr. 10, 2009

(87) PCT Pub. No.: WO2008/044849
PCT Pub. Date: Apr. 17, 2008

(65) Prior Publication Data
US 2010/0044588 A1    Feb. 25, 2010

(30) Foreign Application Priority Data
Oct. 10, 2006    (KR) .................. 10-2006-0098433

(51) Int. Cl.
*C02F 1/32* (2006.01)
(52) U.S. Cl. ..................... 250/455.11; 433/97
(58) Field of Classification Search ............. 250/455.11; 433/97; 422/24
See application file for complete search history.

(56) References Cited

U.S. PATENT DOCUMENTS

| | | | | |
|---|---|---|---|---|
| 4,446,016 A | * | 5/1984 | Stubbs | 210/86 |
| 5,017,135 A | * | 5/1991 | Meyer | 433/92 |
| 5,208,461 A | * | 5/1993 | Tipton | 250/436 |
| 6,464,499 B1 | * | 10/2002 | Lu | 433/92 |
| 2002/0088051 A1 | * | 7/2002 | Nunez | 4/679 |
| 2002/0096648 A1 | * | 7/2002 | Kaiser et al. | 250/492.1 |
| 2011/0008205 A1 | * | 1/2011 | Mangiardi | 422/23 |

FOREIGN PATENT DOCUMENTS

| | | | |
|---|---|---|---|
| JP | 62282686 A | * | 12/1987 |
| JP | 07275272 A | * | 10/1995 |

OTHER PUBLICATIONS

Wastewater. Wordnet 3.0 Princeton University. Jan. 28, 2011. Dictionary.com http://dictionary.reference.com/browse/wastewater.*

* cited by examiner

*Primary Examiner* — Jack Berman
*Assistant Examiner* — Eliza Osenbaugh-Stewart
(74) *Attorney, Agent, or Firm* — John K. Park; Park Law Firm

(57) ABSTRACT

Disclosed therein is a sterilizer for dental contaminants, which can prevent contamination occurring by the surface or a discharge hole of a cuspidor and a discharge hole of a suction mounted on a side of a dental unit chair used to spit out contaminants, such as blood or pus, remaining in a patient's mouth during a dental treatment. The sterilizer includes: a lid having a size as large as to cover an entrance portion of the cuspidor; an ultraviolet lamp mounted on the inner surface of the bottom of the lid; an opening and closing means connected to the lid for opening and closing the lid; and a control part for opening and closing the lid through the opening and closing means and controlling the turning on and off of the ultraviolet lamp. Additionally, in another aspect, the sterilizer may include: a body part for storing contaminants therein; an inlet part connected to a discharge hole of the cuspidor or a suction for transferring the contaminants to the body part; an outlet part connected to a drain pipe for discharging the contaminants stored in the body part to the drain pipe; and a ultraviolet lamp mounted inside the body part and having a light-emitting portion.

3 Claims, 4 Drawing Sheets

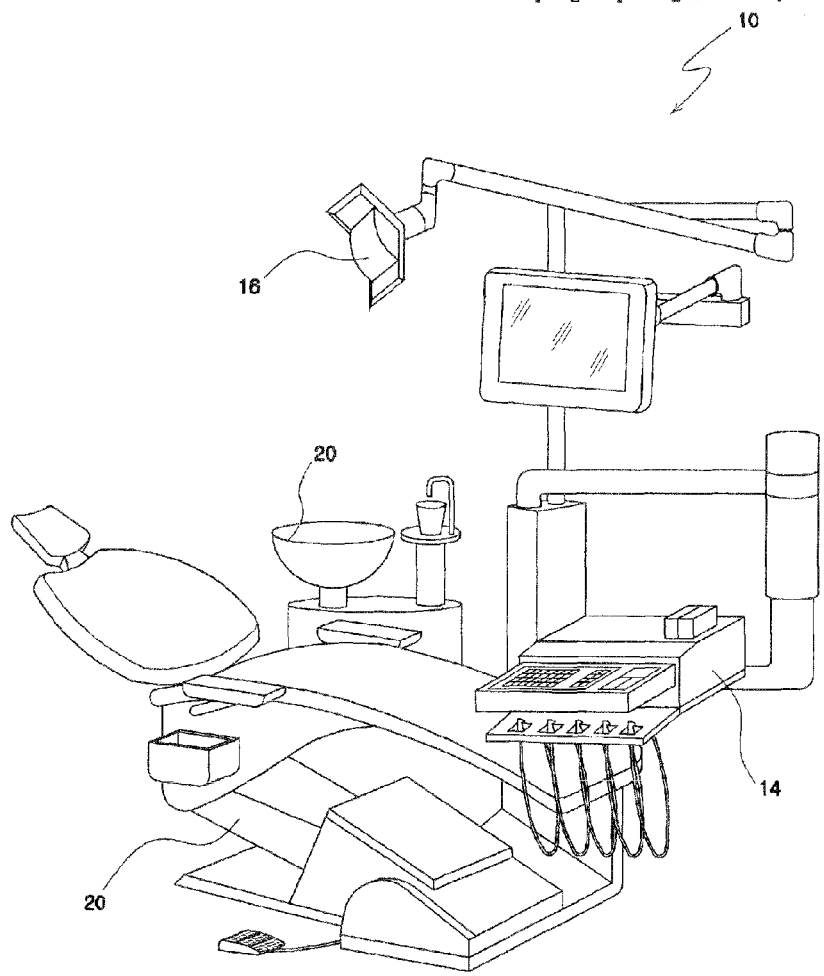
[Fig. 1] Prior Art
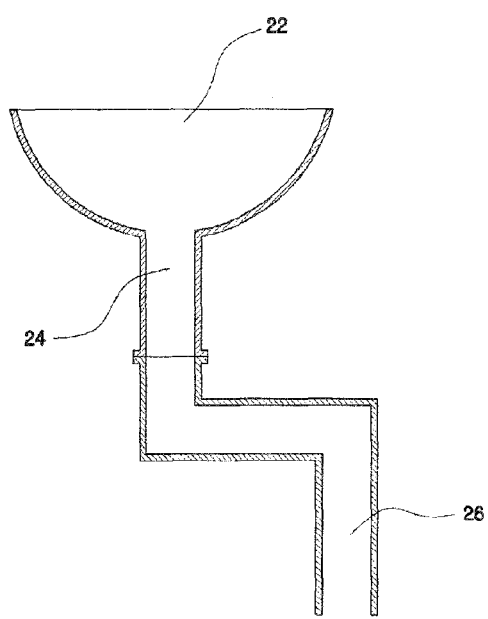
[Fig. 2] Prior Art

[Fig. 3]
(a)
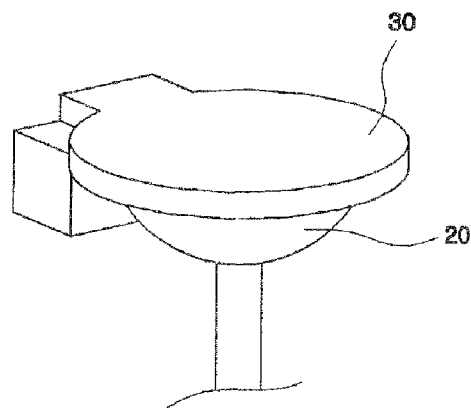
(b)
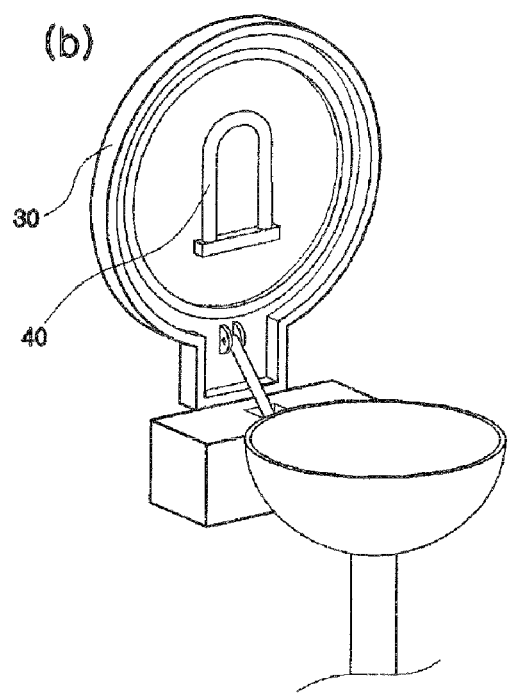
(c)
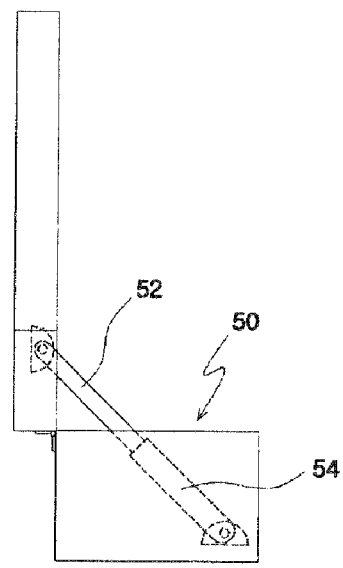

[Fig. 4]
(a)
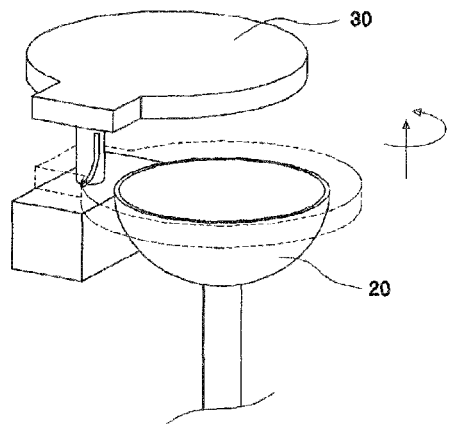
(b)
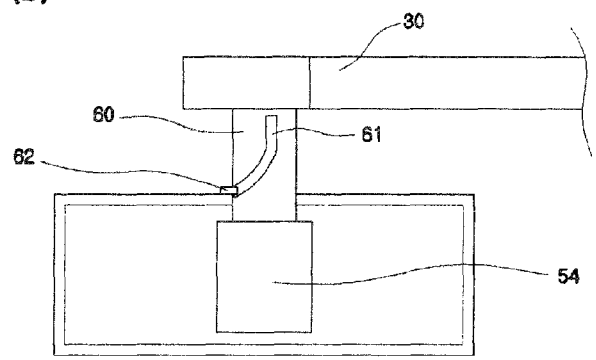
[Fig. 5]
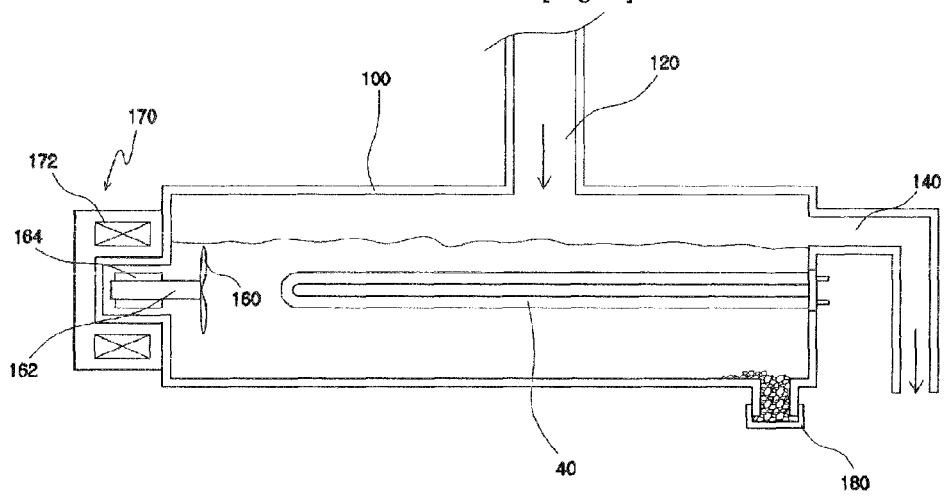

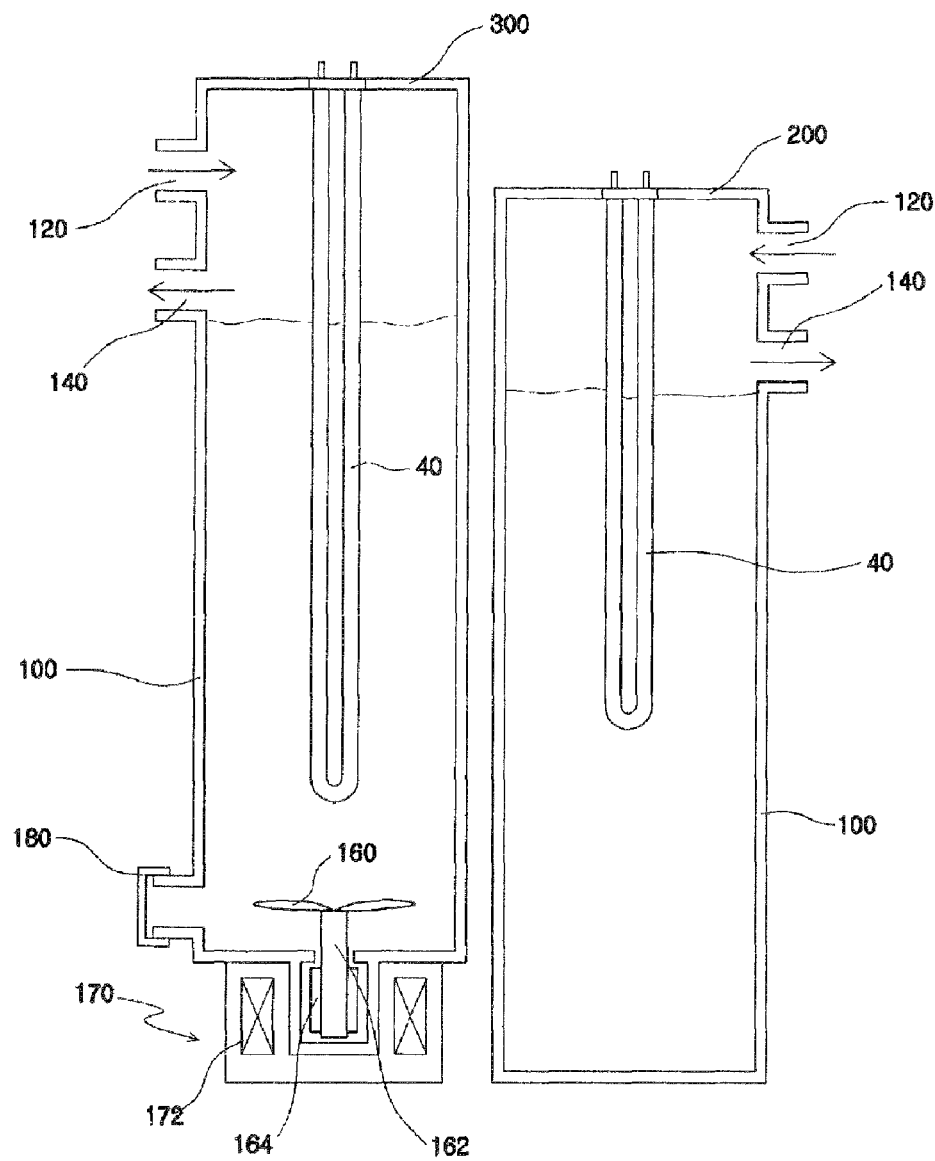
[Fig. 6]

STERILIZER FOR DENTAL CONTAMINANT

TECHNICAL FIELD

The present invention relates to a sterilizer for dental contaminants, and more particularly, to a sterilizer for dental contaminants, which can prevent contamination occurring by the surface or a discharge hole of a cuspidor and a discharge hole of a suction mounted on a side of a dental unit chair used to spit out contaminants, such as blood or pus, remaining in a patient's mouth during a dental treatment.

BACKGROUND ART

Recently, as medical accidents caused by infection during a dental treatment was reported through broadcasting, an interest in dental treatment tools and environments of a consultation room are being increased.

According to information, which has been known till now, including the above reported data, there are 3 million to 4 million bacteria of more than 500 kinds per □ in a human being's mouth, and 10 million to 32 million bacteria per □ in a patient, who has an inflammation in his or her mouth, and in a terrible case, molds and staphylococci are found in the mouth.

In addition, even though 840,000 bacteria exist in the inside air of the consultation room of a dental clinic, since precaution or post measure is not took thoroughly, cases that patients get AIDS or are infected by germs frequently break out.

Korean Patent Nos. 457,467 and 457,860 disclose sterilizers to sterilize a handpiece, which is a representative dental treatment tool, to solve the contamination of the dental treatment instruments. The patented sterilizers can sterilize treatment tools, which were in contact with a patient's mouth, and disinfect bacteria spreading in the consultation room through the treatment tools.

As shown in FIG. 1, a unit chair 10 generally used for a dental treatment includes a chair body 12, a treatment tool holder 14, an illumination lamp 16, and a cuspidor 20.

As shown in FIG. 2, the cuspidor includes a wide entrance portion 22, a discharge hole 24 for discharging contaminants, which the patient spits into the entrance portion 22, to the outside of the cuspidor, and a drain pipe 26 connected to the discharge hole.

Furthermore, the unit chair 10 further includes a suction (not shown) mounted on a side thereof for sucking the contaminants, such as spit and blood, gathered in the patient's mouth during the dental treatment, and the contaminants sucked into the suction are discharged to the drain pipe through an additional pipe.

However, contaminants such as biological tissues, saliva, tooth fragments or prosthetic material powder inevitably generated during the dental treatment process remain in the patient mouth, and such contaminants are spat out to the cuspidor or discharged to the outside through the suction during a process of cleaning the patient's mouth. So, the cuspidor and the drain pipe connected to the cuspidor or the suction are contaminated.

To prevent contamination of the surface of the cuspidor and the drain pipes connected to the cuspidor and the suction, it is general to sterilize the surface of the cuspidor or the suction with an antiseptic solution. In addition, Korean Utility Model Registration No. 403,843 discloses an antibacterial cuspidor containing nano-silver material for preventing infection through the nano-silver material coated thereon.

However, the prior art has several problems in that if a sterilized cleaning solution is used, the cleaning solution mixed with foreign substances may cause environmental pollution, and in that there is a great adverse criticism against the sterilization effect of the nano-silver coating and it is difficult to obtain a perfect sterilization effect just by coating the cuspidor with the nano-silver material.

DISCLOSURE OF INVENTION

Technical Problem

Accordingly, the present invention has been made to solve the above-mentioned problems occurring in the prior arts, and it is an object of the present invention to provide a sterilizer for dental contaminants, which can sterilize a cuspidor with ultraviolet rays, prevent contamination of air generated by the cuspidor by covering a lid thereon, and sterilize the contaminants discharged from the cuspidor mixed with foreign substances to thereby prevent an environmental problem.

It is another object of the present invention to provide a sterilizer for dental contaminants, which is convenient to use since an operator, such as a doctor or a nurse, or a patient can automatically open and close the sterilizer, which is opened and closed in such a way as not to be in contact with the patient, and which prevents a leakage of ultraviolet rays to the outside during sterilization.

It is yet another object of the present invention to provide a sterilizer for dental contaminant, which can sterilize bacteria at discharge holes connected to the cuspidor and a suction to thereby reduce infection by the contaminants through the discharge holes.

Technical Solution

To achieve the above objects, the present invention provides a sterilizer for dental contaminants for sterilizing a cuspidor fixedly mounted to a dental unit chair, comprising: a lid having a size as large as to cover an entrance portion of the cuspidor; an ultraviolet lamp mounted on the inner surface of the bottom of the lid; an opening and closing means mounted on the outer surface of the cuspidor fixedly mounted to the dental unit chair and connected to the lid for opening and closing the lid; and a control part for opening and closing the lid through the opening and closing means and controlling the turning on and off of the ultraviolet lamp.

It is preferable that the lid can be opened and closed by an operational rod connected to an operating mechanism mounted inside the opening and closing means.

In addition, it is preferable that the opening and closing means includes: a guide rod connected integrally with the lid and having a guide groove or a guide protrusion for allowing rising and rotation of the lid; a guide member having a guide protrusion or a guide groove coupled with the guide groove or the guide protrusion; and the operating mechanism for operating the guide rod.

Furthermore, in another aspect of the present invention, the present invention provides a sterilizer for dental contaminants, which has the same technical idea in that it sterilize contaminants with ultraviolet rays and is mounted on a discharge hole of a cuspidor or a suction, comprising: a body part for storing contaminants therein; an inlet part connected to a discharge hole of the cuspidor or a suction for transferring the contaminants to the body part; an outlet part connected to a drain pipe for discharging the contaminants stored in the body part to the drain pipe; and a ultraviolet lamp mounted inside the body part and having a light-emitting portion.

Moreover, it is preferable that the sterilizer further comprises a stirrer having stirring wing for stirring the contaminants stored in the body part and a driving portion for rotating the stirring wing.

In addition, it is preferable that the sterilizer further comprises a foreign substance-removing part mounted on the lower end of the body part and tightly sealed with an openable lid.

As described above, the two cuspidor sterilizers can be separately or all mounted on the cuspidor since their mounting locations are different from each other.

ADVANTAGEOUS EFFECTS

The sterilizer for dental contaminants according to the present invention can sterilize a cuspidor with ultraviolet rays, prevent contamination of air generated by the cuspidor by covering a lid thereon, and sterilize contaminants discharged from the cuspidor mixed with foreign substances to thereby prevent an environmental problem.

Furthermore, the sterilizer for dental contaminants is convenient to use since the operator, such as the doctor or the nurse, or the patient can automatically open and close the sterilizer, and can prevent a leakage of ultraviolet rays to the outside during sterilization and sterilize bacteria at discharge holes connected to the cuspidor and a suction to thereby reduce infection by the contaminants through the discharge hole.

BRIEF DESCRIPTION OF THE DRAWINGS

FIG. 1 is a view of a dental unit chair.
FIG. 2 is a view showing a form of a typical cuspidor.
FIG. 3 is a view of a sterilizer for dental contaminants according to the present invention.
FIG. 4 is a view of another sterilizer for dental contaminants according to the present invention.
FIG. 5 is a view of a further sterilizer for dental contaminants according to the present invention.
FIG. 6 is a view of a still further sterilizer for dental contaminants according to the present invention.

MODE FOR THE INVENTION

Reference will be now made in detail to the preferred embodiment of the present invention with reference to the attached drawings.

First Embodiment

A sterilizer for sterilizing the surface of a cuspidor according to a first preferred embodiment of the present invention includes: a lid 30 for sealing an entrance portion 22 of the cuspidor 20; an ultraviolet lamp 40 mounted on the inner surface of the bottom of the lid 30; an opening and closing means 50 connected to the lid 30 for opening and closing the lid 30; and a control part (not shown) for controlling operations of the opening and closing means 50 and the ultraviolet lamp 40.

The lid 30 has a size as big as it can cover the entrance portion 22 of the cuspidor 20 and has the ultraviolet lamp 40 mounted on the inner surface of the bottom thereof, so that it can sterilize the surface of the contaminated cuspidor 20 when the lid 30 covers the entrance portion 22 and the ultraviolet lamp 40 emits ultraviolet rays.

During a dental treatment, the sterilizer according to the present invention includes the opening and closing means 50 for opening the lid 30 when a patient wants to spit out foreign substances remaining in the patient's mouth and closing the lid 30 when the patient does not so.

The opening and closing means 50 serves to open the lid to avoid interference when the patient uses the cuspidor.

The opening and closing means 50 shown in FIG. 3 is constructed in such a way that the lid 30 is opened and closed by an operational rod 52 connected to an operating mechanism 54.

The opening and closing means 50 shown in FIG. 3 may adopt any one of a link, a rotational motor, and others connected to one of a pneumatic cylinder, a linear motor and a rotational motor, which can operate the operational rod 52 in an opening and closing direction of the lid 30, to thereby convert a rotational motion of the rotational motor into a rectilinear motion.

In addition, as shown in FIG. 4, it is preferable that the opening and closing means 50 includes: a guide rod 60 connected integrally with the lid 30 and having a guide groove 61 for allowing rising and rotation of the lid 30; a guide member having a protrusion 62 coupled with the guide groove 61; and the operating mechanism 54 for operating the guide rod 60.

In this instance, also the operating mechanism 54 for operating the guide rod 60 may adopt any one of a link, a rotational motor, and others connected to one of a pneumatic cylinder, a linear motor and a rotational motor, which can operate the guide rod 60 in a straight line, to thereby convert a rotational motion of the rotational motor into a rectilinear motion. Of course, the guide rod 60 and the operating mechanism 54 shown in FIG. 4 must be connected to each other in such a way as not to interrupt the rotation of the guide rod 60.

The control part (not shown) serves to open and close the lid 30 by the opening and closing means 50, sterilize the surface of the cuspidor by turning on the ultraviolet lamp 40 when the lid 30 is closed, and turn off the ultraviolet lamp 40 when the lid 30 is opened. The operation of the control part can be achieved in such a way that an operator, such as a doctor or a nurse, manipulates a switch (not shown) or a patient presses a push switch (not shown) mounted on a back rest of the dental unit chair.

The contaminant sterilizer according to the first preferred embodiment of the present invention can be directly mounted on the cuspidor or mounted on a structure installed on the floor. In this embodiment, a description of wiring for supplying electricity or pneumatic pressure necessary to operate the operating mechanism and the ultraviolet lamp is omitted, but those skilled could realize the present invention through the above description without any difficulty.

Second Embodiment

As shown in FIGS. 5 and 6, a sterilizer for sterilizing contaminant discharged through an outlet of a cuspidor or a suction includes: a body part 100 for storing contaminants therein; an inlet part 120 formed on the body part 100 and connected to the discharge hole of the cuspidor or the suction for transferring contaminants to the body part 100; an outlet part 140 formed on the body part 100 and connected to a drain pipe for discharging the contaminants stored in the body part 10 to the drain pipe; and a ultraviolet lamp 40 having a light-emitting portion formed therein for sterilizing the contaminants stored in the body part 100.

In addition, it is preferable that the sterilizer further includes a stirrer having stirring wing 160 for stirring the contaminants stored in the body part 100 and a driving portion 170 for rotating the stirring wing 160.

In FIG. 5, the driving portion 170 for rotating the stirring wing 160 includes a permanent magnet 164 mounted around a shaft 162 of the stirring wing 160 and an electromagnet 172 mounted on the outer surface of the body part 100 for transferring a driving force to the permanent magnet 164, so that the driving portion 170 can rotate the stirring wing 160 by applying electric current to the electromagnet 172 like a general motor. As described above, when the stirring wing 160 is rotated, the contaminants are circulated and evenly exposed to the ultraviolet rays to thereby being sterilized.

In this embodiment, the stirrer shown in FIG. 5 has been described, but it is possible to stir the contaminants by attaching the stirring wind 160 to a submergible motor or it is also possible that a magnetic substance is mounted on the stirring wing and a permanent magnet is mounted on the outer surface of the body part to thereby rotate the stirring wing by the rotation of the permanent magnet.

Moreover, it is preferable that the sterilizer further includes a foreign substance-removing part mounted on the lower end of the body part 100 and tightly sealed with an openable lid 180. Tooth tissues or metallic foreign substances out of contaminants discharged to the discharge hole through the foreign substance-removing part are accumulated. So, it is preferable to periodically remove the accumulated contaminants.

If the stirring wing 160 induces a movement of the contaminants in a direction of the foreign substance-removing part, heavy contaminants, which are not discharged to the outlet part, can be more easily accumulated at the foreign substance-removing part.

FIG. 6 illustrates contaminant sterilizers separately mounted on the discharge holes of the cuspidor and the suction. The sterilizer 300 connected to the discharge hole of the cuspidor includes all components shown in FIG. 5, but the sterilizer 200 connected to the discharge hole of the suction includes the body part 100, the inlet part 120, the outlet part 140 and the ultraviolet lamp 40.

The sucked contaminants are discharged with a strong pressure at the suction and the inlet part 120 of the sterilizer 200, and thereby, the contaminants stored in the body part 100 are moved. So, the stirrer is not needed.

INDUSTRIAL APPLICABILITY

As described above, the sterilizer for dental contaminants according to the present invention can prevent contamination occurring by the surface or the discharge holes of the cuspidor and the suction mounted on a side of the dental unit chair used to spit out the contaminants, such as blood or pus, remaining in the patient's mouth during the dental treatment.

The invention claimed is:

1. A sterilizer for dental contaminants for sterilizing a cuspidor fixedly mounted to a dental unit chair, comprising: a lid having a size as large as to cover an entrance portion of the cuspidor; an ultraviolet lamp mounted on the inner surface of the bottom of the lid; an opening and closing means mounted on the outer surface of the cuspidor fixedly mounted to the dental unit chair and connected to the lid for opening and closing the lid; and a control part for opening and closing the lid through the opening and closing means and controlling the turning on and off of the ultraviolet lamp.

2. The sterilizer for dental contaminants according to claim 1, wherein the lid is opened and closed by an operational rod connected to an operating mechanism mounted inside the opening and closing means.

3. The sterilizer for dental contaminants according to claim 1, wherein the opening and closing means includes: a guide rod connected integrally with the lid and having a guide groove or a guide protrusion for allowing rising and rotation of the lid; a guide member having a guide protrusion or a guide groove coupled with the guide groove or the guide protrusion; and the operating mechanism for operating the guide rod.

* * * * *